US 6,949,065 B2

(12) United States Patent
Sporer et al.

(10) Patent No.: US 6,949,065 B2
(45) Date of Patent: Sep. 27, 2005

(54) LEFT VENTRICULAR ASSIST SYSTEM

(75) Inventors: Norbert Sporer, Wielenbach (DE); Harald Wagner, Seefeld (DE); Thomas Schmid, Bernried (DE); Wolfgang Schiller, Bonn (DE)

(73) Assignee: Deutsches Zentrum für Luft-und Raumfahrt e.V., Bonn (DE)

( * ) Notice: Subject to any disclaimer, the term of this patent is extended or adjusted under 35 U.S.C. 154(b) by 400 days.

(21) Appl. No.: 10/126,978

(22) Filed: Apr. 22, 2002

(65) Prior Publication Data
US 2002/0165426 A1 Nov. 7, 2002

(30) Foreign Application Priority Data
Apr. 20, 2001 (DE) .......................................... 101 19 691

(51) Int. Cl.[7] .............................................. A61N 1/362
(52) U.S. Cl. ....................................... 600/16; 623/3.16
(58) Field of Search .................. 600/16; 623/3.16–3.19

(56) References Cited

U.S. PATENT DOCUMENTS 5,314,469 A * 5/1994 Gao .......................... 623/3.18
5,473,302 A * 12/1995 Terlop et al. ................ 336/183
5,704,891 A * 1/1998 Mussivand .................... 600/16
5,964,694 A * 10/1999 Siess et al. .................... 600/17
6,264,601 B1 * 7/2001 Jassawalla et al. ........... 600/16
6,330,910 B1 * 12/2001 Bennett ....................... 165/297

* cited by examiner

Primary Examiner—George Manuel
(74) Attorney, Agent, or Firm—Browdy and Neimark, PLLC

(57) ABSTRACT

A fully implantable left ventricular assist system comprising a pumping means connectable via adapter elements to the ventricle includes two compressible chambers in the form of sacs (5, 5') and a compressing means (4) to alternatingly fill and discharge the compressible chambers (5, 5') at the same time, including a drive unit (41) assigned thereto, a cooling means (50) for cooling the drive unit (41), and a power supply unit (60) for the drive unit (41) and cooling means (50).

In this implantable system the pumping means, compression means (4), drive unit (41) and part of the cooling means (50) are accommodated in a two-part housing (1) on which tubular ports (10*a*, 10*b*; 10'*a*, 10'*b*) for connecting Y-shaped adapter elements (3, 3') are configured.

11 Claims, 9 Drawing Sheets

LEFT VENTRICULAR ASSIST SYSTEM

The invention relates to a left ventricular assist system.

Cardiovascular diseases have since become the number one fatality in western industrial nations. Implantable mechanical ventricular assist devices (VAD) have been in use now clinically for some 20 years. This form of therapy mainly serves as a bridge to transplant when no donor organ is available or the patient is already in such a critical health condition that he would in all probability fail to survive the acute stress of a heart transplantation and the initial high-dosis immune suppressive therapy involved.

Then—following stabilization over several months by a VAD with an improvement in the organ functions detrimented previously by acute or chronic diminished circulation—the patients can be admitted to the transplantation with a higher anticipated success. More recent results have shown that the functioning of the heart may be improved by this therapy to such an extent that there is a possibility of system explantation without a subsequent heart transplantation (bridge to recovery).

Due to the lack of donors and organ allocation in accordance with a waiting list early or, in some cases, premature application for transplantation is experienced which results in suboptimal organ allocation. By making use of suitable heart assist systems on a full-scale basis available donor organs could be optimally allocated by eliminating a waiting list calculation and the result of the heart transplantation could be improved on recovery of the organ functioning following mechanical ventricular assist.

Frequent application is, however, counteracted by the serious complications of this form of therapy such as above all thromboembolies and their serious consequences such as, for example, hemiplegia following apoplexy. To prevent thrombosis the coagulation of the blood needs to be blocked by medication which in turn results in bleeding complications.

Furthermore, most of these systems require venting which is usually achieved by a transcutaneous vent, i.e. a tube originating in the assist system and led out through the abdominal skin to admit the inflow of air through a filter. In addition to this, the patient also needs to carry with him leads connecting an external battery and control unit.

This, on the one hand, handicaps the patient, since he is made continually aware of being dependent on a mechanical pump, and, on the other, this represents at the same time an entry portal for germs. A further problem is heat dissipation. Commercially available VADs can now be implanted in some patients for as long as four years, however, a permanent solution is not yet available.

Counted as one of the most proven systems technically hitherto implanted in a human is the NOVACOR 100 (P) system made by the Novacor Division, Baxter Healthcare Corp., Oakland/Calif., USA. In this Novacor system only the pump is implanted; power supply and electronic controller are carried extracorporeal also in this system.

Since in the aforementioned Novacor system venting is done with a tube directly through the skin, complications due to infections may occur more pronouncedly. In addition, problems are encountered due to moisture forming from implantation of a vent receptacle.

In the Novacor system to dissipate the heat a transcutaneous tube is used at the expense of having to accept a much higher risk of infection which is furthermore aggravated by the problem of the power supply and communicating process data likewise being solved hitherto by a transcutaneous cable connection.

Furthermore, the systems employed hitherto are too bulky and thus cannot be implanted, or only with difficulty, in children or small people. This is why the left ventricular assist has been implemented hitherto only with single-chamber systems. In addition, employing more than two aortic valve prosthetics in a heart assist system considerably influences the circulatory haemodynamics, necessitating the use of anticoagulants. Form and pumping principle of known pumps employed to date produce flow conditions detrimental to red blood cells (erythrocytes).

The reason for damage to the blood cells is always, however, excessive fluid shear resulting from instationary and turbulent flow conditions, producing a deformation and ultimately destruction of the membrane of the red blood cells. So-called dead water areas in the further course of the flow additionally prompt deposition and sticking of defective cells which in turn results in thrombosis.

It is thus the objective of the invention to provide a fully implantable left ventricular assist system posing a low risk of thrombosis sufficing without a vent and without transcutaneous wiring.

In accordance with the invention this objective for a left ventricular assist system is achieved by the features as set forth in claim 1. Advantageous further embodiments are the subject matter of claims relating back to claim 1 directly or indirectly.

In accordance with the invention the left ventricular assist system comprising a pumping means, a cooling means and a power supply means can be implanted as a whole. Unlike the majority of systems employed hitherto the pumping means comprises two pumping chambers and only three valves. In addition to two aortic valve prosthetics a so-called sail valve is provided at the outlet of the assist system in accordance with the invention, this being the reason why the complete system works considerably less damaging to the blood than all systems known to date. Due to its compact design the assist system in accordance with the invention can be implanted in small people as well as in children.

The system in accordance with the invention is thus not only full implantable, it is also optimized haemodynamically. Furthermore the assist system in accordance with the invention comprises two flow-optimized pumping chambers, of which the one is primed similar in strength to that with which the other outputs its blood volume. This results in the left ventricle receiving maximum relief and thus also in relief of the pulmonary flow and of the right heart. More particularly this simultaneous expulsion and priming action results in the intracavitary volume remaining constant in thus eliminating the need for a vent.

Implanting the assist system in accordance with the invention with all necessary components in the body of a patient enhances quality of life whilst minimizing the risk of infection, if not excluding this risk altogether.

The invention will now be detailed with reference to the drawings in which.

Figure 1:
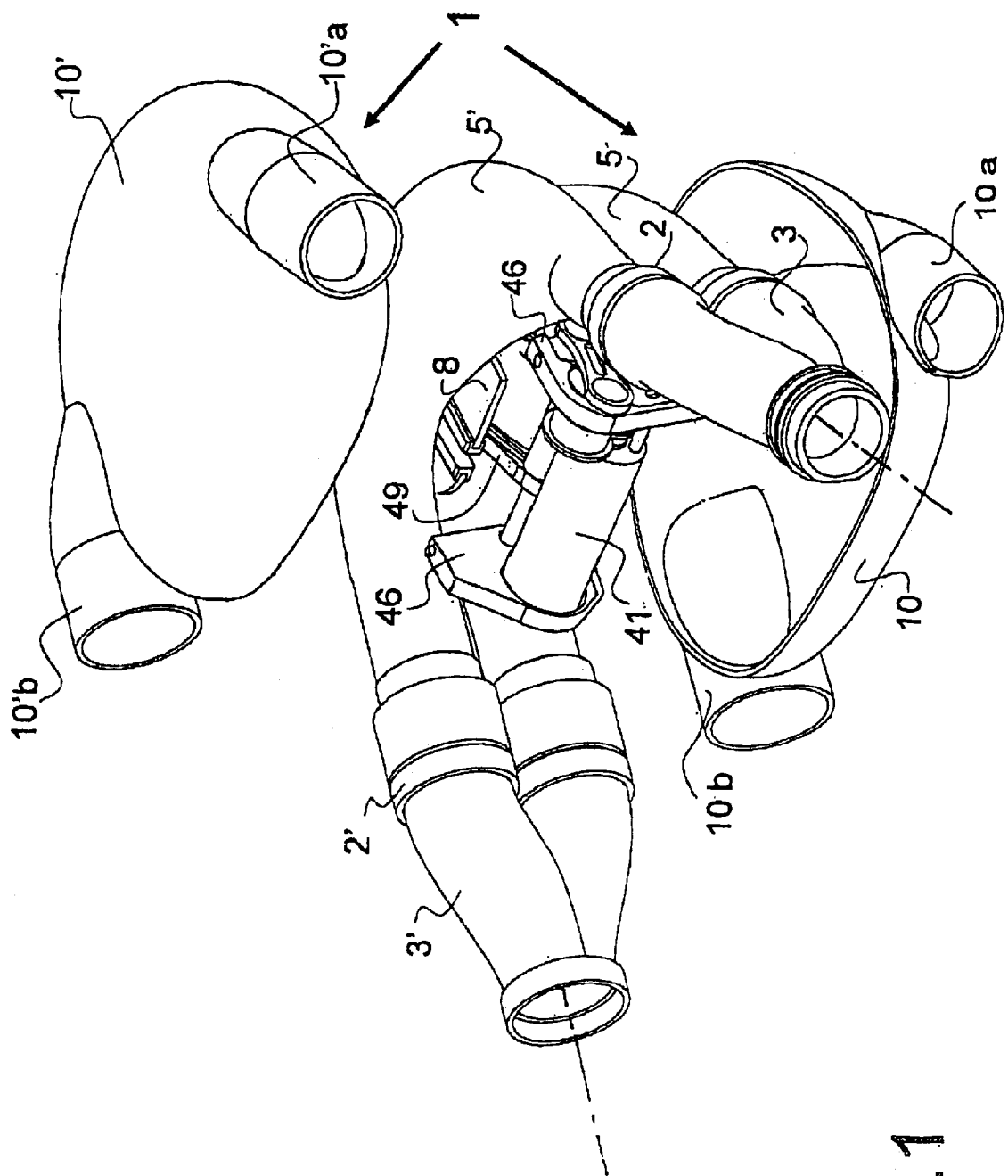
FIG. 1 is a view in perspective of a means including two chambers accommodated in a housing for use as a so-called blood pump.

Referring now to FIG. 1 there is illustrated a view in perspective of a means for use as a so-called blood pump to be accommodated in a housing 1 comprising two housing halves 10 and 10'. Configured at each of the two housing halves 10 and 10' are two tubular ports 10a and 10b and 10a' and 10'b respectively.

Illustrated between the two housing halves 1 and 1' are two chambers configured one above the other as sacs 5 and 5' connected to each other via Y-shaped adapters 3 and 3'. Details as to the type and arrangement available of the sacs 5, 5' are described with reference to FIGS. 4 and 5.

Figure 8:
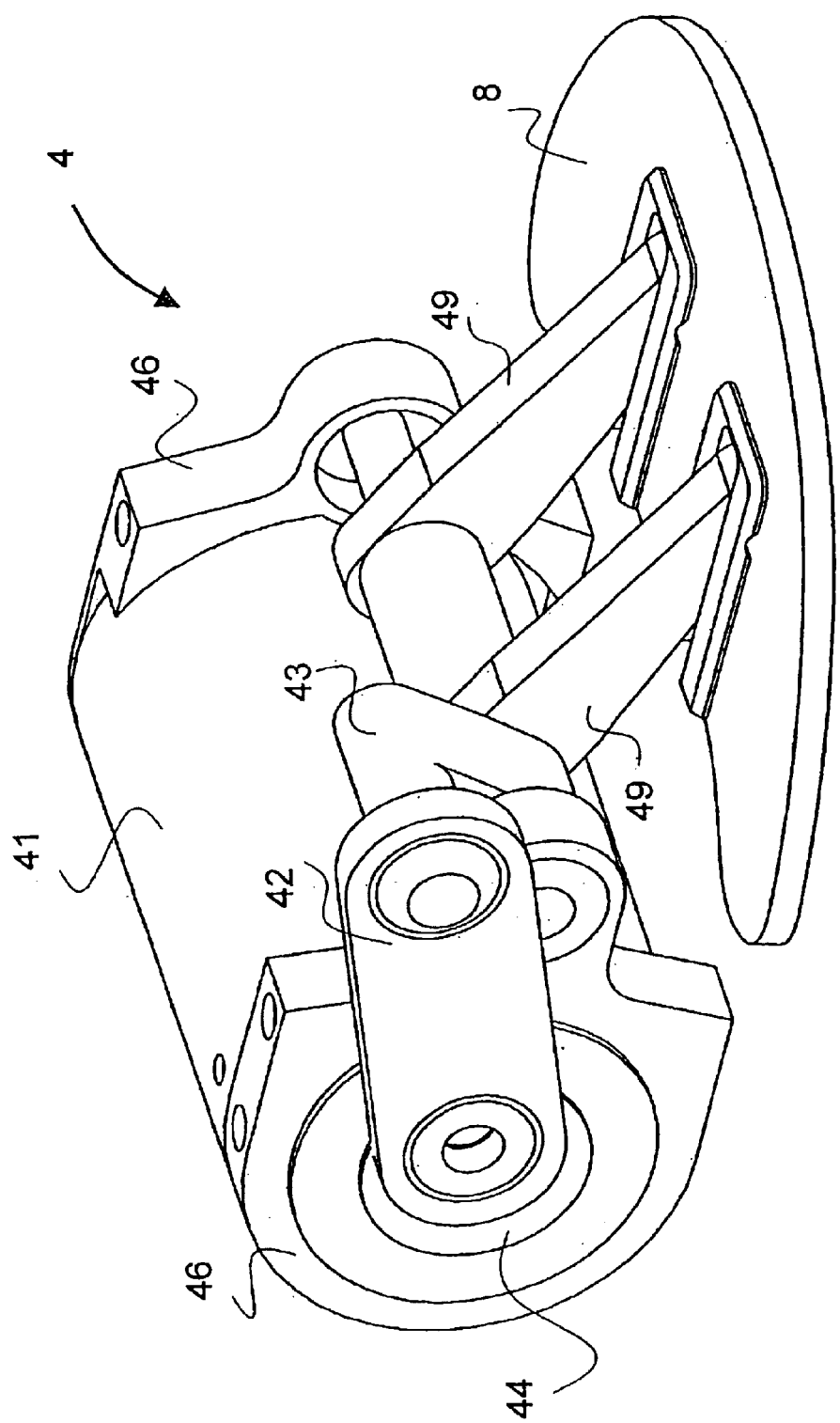
FIG. 8 is a view in perspective of a mounted cooling means.

Provided between the two sacs 5 and 5' is a plate 8 exerting a pushing action, termed pusher plate 8 in the following, and which is part of a compression means 4 configured as a module described in detail in the following with reference to FIG. 3 and FIG. 8. Via side mounts 46 the compression means 4 is supported in the two housing halves 10 and 10' by ways and means not shown in FIG. 1 in thus being precisely located in place.

Provided between the sacs 5 and 5' and the Y-shaped adapters 3 and 3' are adapter parts 2 and 2' respectively as described in detail with reference to FIGS. 6 and 7. The adapter parts 2 and 2' are secured in the housing 1 at the ports 10a and 10a' and 10b and 10'b respectively. From within the housing the sacs 5 and 5' are secured to the adapter parts 2 and 2'. When the housing halves 10 and 10' are joined together into a closed housing 1 the Y-shaped adapters 3 and 3' are mounted from without on the adapter parts 2 and 2' respectively and located in place thereon.

Figure 3:
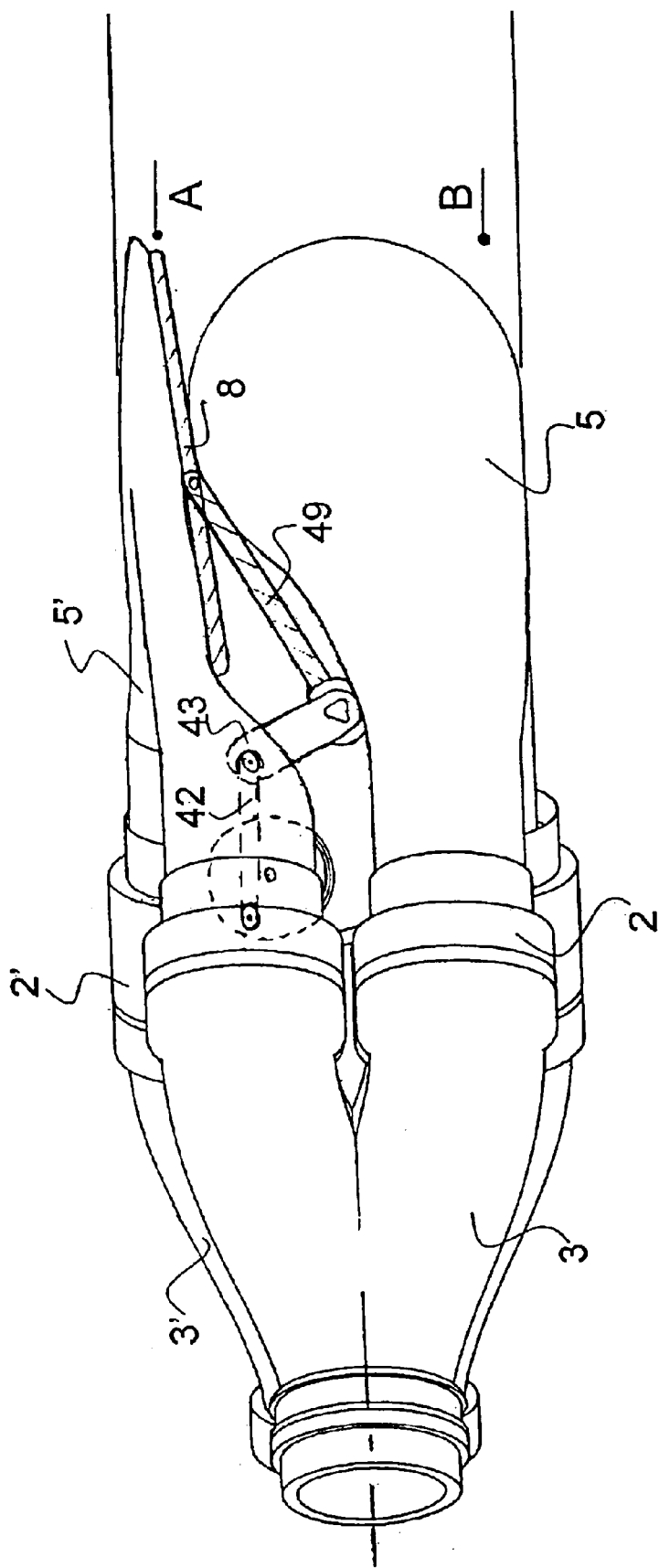
FIG. 3 is a further view in perspective of the means for use as a blood pump.

By alternatingly compressing one of the sacs 5, 5' fluid (blood) is pumped proximally whilst releasing the other sac simultaneously priming the fluid, resulting in the pusher plate 8 being reciprocated between end positions A and B at a uniform rate or accelerated (see FIG. 3).

Figure 2A:
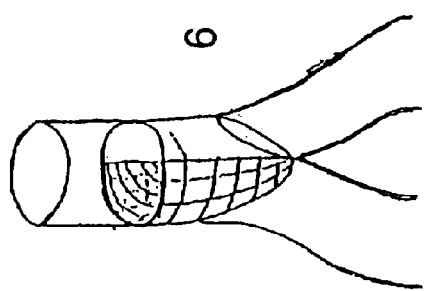
FIGS. 2a and 2b are each a diagrammatic view of the pumping principle for two chambers with three valves.

Referring now to FIG. 2 there is illustrated in a diagrammatic view how compressing the sac 5 results in pressure being built-up therein; at the same time a valve V1 is closed at the inlet. It is this pressure build-up in the sac 5 that causes a sail valve 6 to flap into the position as shown in FIG. 2a. This results in the fluid contained in the sac 5 being expelled as indicated by the arrow P1 in FIG. 2a until the pusher plate 8 has attained the end position A (FIG. 3).

This flapping action of the sail valve 6 closes the outlet of the sac 5', causing a vacuum to materialize therein, causing valve V2 to open and fluid (blood) to flow into the sac 5' as indicated by the arrow P2 in FIG. 2a. As soon as the pusher plate 8 has attained the end position A the sac 5 is practically empty whilst the sac 5' has become full.

Figure 2B:
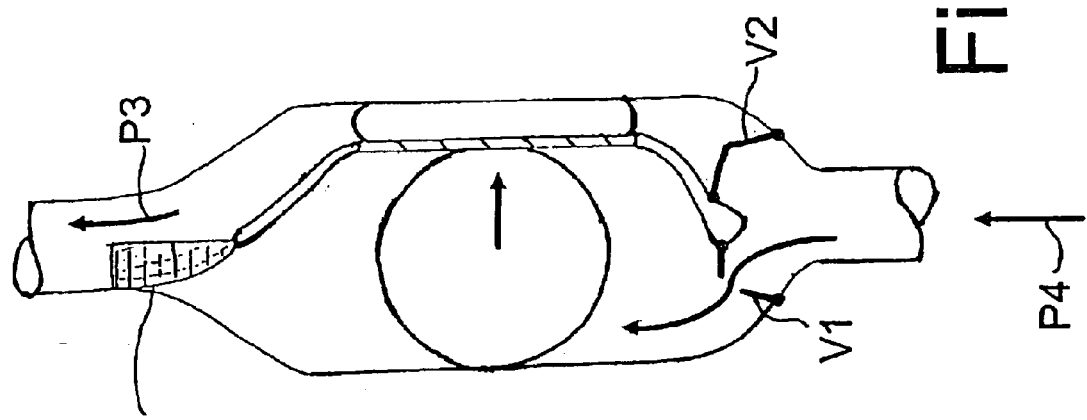

When the pusher plate 8 is then moved from the end position A in the direction of the end position B the sail valve 6 flaps back into the position as shown in FIG. 2b, resulting in valve V2 closing and valve V1 opening. The fluid (blood) in sac 5' is expelled therefrom (see arrow P3 in FIG. 2b) and simultaneously fluid primed into sac 5 (see arrow P4 in FIG. 2b) in thereby filling it. The sacs 5, 5' may be connected to the pusher plate 8 mechanically, where necessary, since this permits boosting the vacuum and thus the priming action.

Figure 2C:
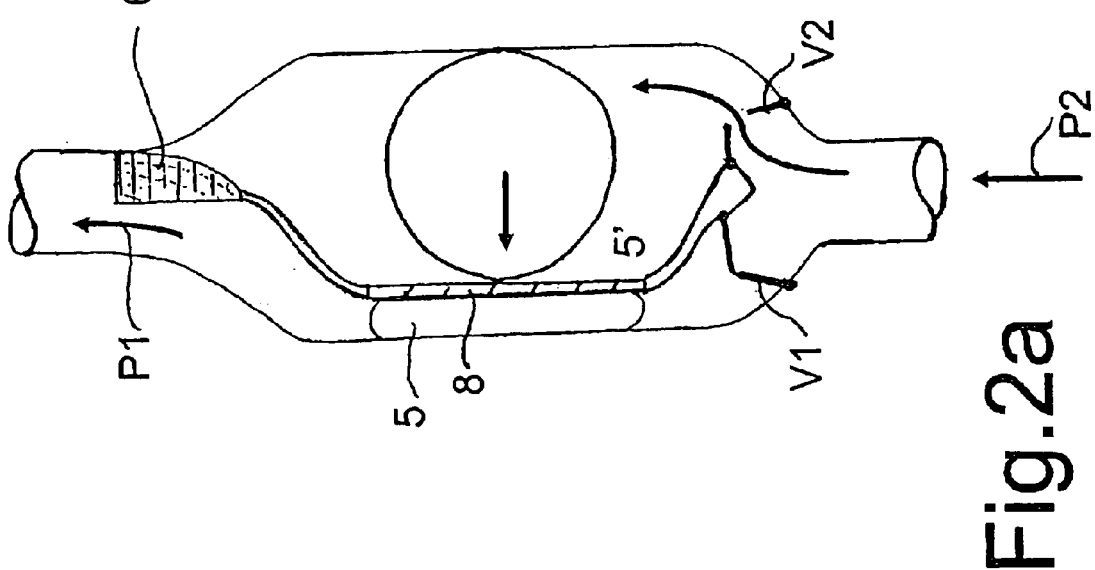
FIG. 2c is a diagrammatic view on a magnified scale of a sail valve.

Referring now to FIG. 2c there is illustrated a flap-type sail valve 6. Conventional aortic valve prosthetics are/may be used as valves V1 and V2.

Referring now to FIG. 3 there is illustrated a pumping means serving as the fluid or blood pump. The tubular chambers in the form of sacs 5, 5' are arranged fixedly located opposite each other. The inlets of the sacs 5, 5' are merged by means of the Y-shaped adapter 3. Upstream of each sac 5, 5' a valve is provided in the form of conventional aortic valve prosthetics 25, 25' as detailed with reference to FIGS. 6 and 7. At the outlet the two sacs 5, 5' are merged by means of the Y-shaped adapter 3'. Provided in the adapter 3' is the sail valve 6 as illustrated in FIG. 2c on a magnified scale (not shown in FIG. 3). The sacs 5, 5' may differ in wall thickness.

Provided as the compressing means is a very thin pusher plate 8 rotatably mounted in lever arms 49. By means of a drive unit the lever arms 49 and via these the pusher plate 8 is reciprocated between end positions A and B (FIG. 3), the pusher plate 8 thereby compressing the sacs 5, 5'. In this arrangement the pusher plate 8, which may be configured flexible, can be adapted in its angular setting optimally to the shape of the sac 5 or 5' compressed in each case.

Figure 4:
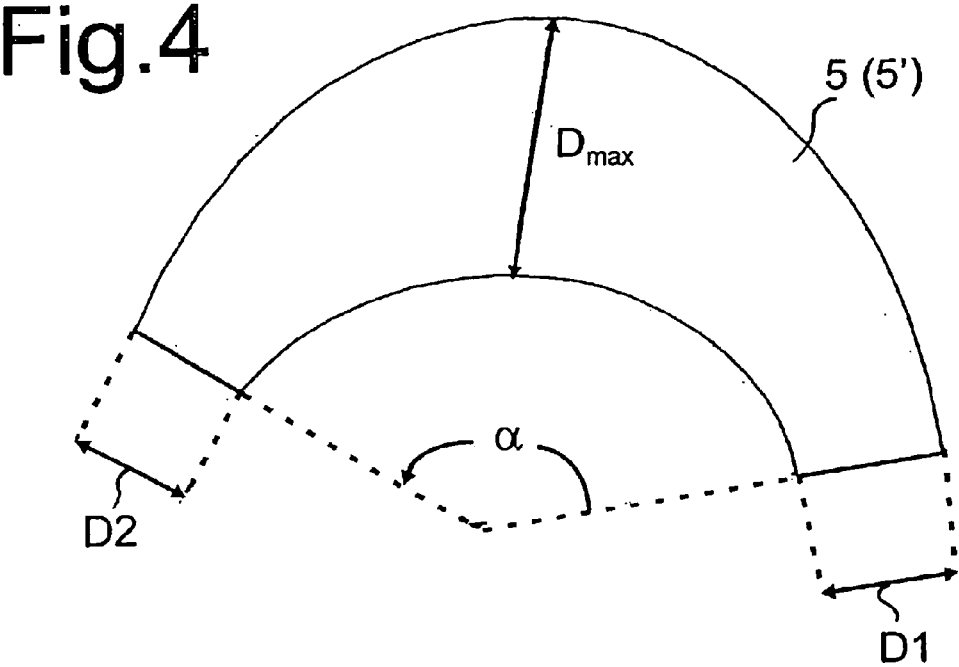
FIG. 4 is a diagrammatic plan view of a chamber in the form of a curved sac.

Referring now to FIG. 4 there is illustrated in a plan view one embodiment of a chamber in the form of, for example, one of the curved sacs 5, 5'; it being the sac geometry which is vital to an optimum flow profile.

The sacs 5, 5' provided for use in a blood pump have an angle of curvature α<180° and are designed so that the diameter D1 of the sacs 5, 5' at the inlet smoothly increases up to a maximum diameter $D_{max}$ before smoothly decreasing to a diameter D2 at the outlet. In this arrangement the maximum diameter $D_{max}$ is not located in the middle between inlet and outlet, but instead nearer to the outlet of each sac 5, 5'; diameter D1 at the inlet side of each sac 5, 5' being preferably somewhat larger than the diameter D2 at the outlet side thereof.

In the two-chamber pump described two preferably identically dimensioned sacs 5, 5' are accommodated located in place mirror-symmetrical to the pusher plate 8 by means of correspondingly dimensioned adapters 3, 3' in the housing 1 formed by the two housing halves 10, 10'. (FIG. 4).

Figure 5:
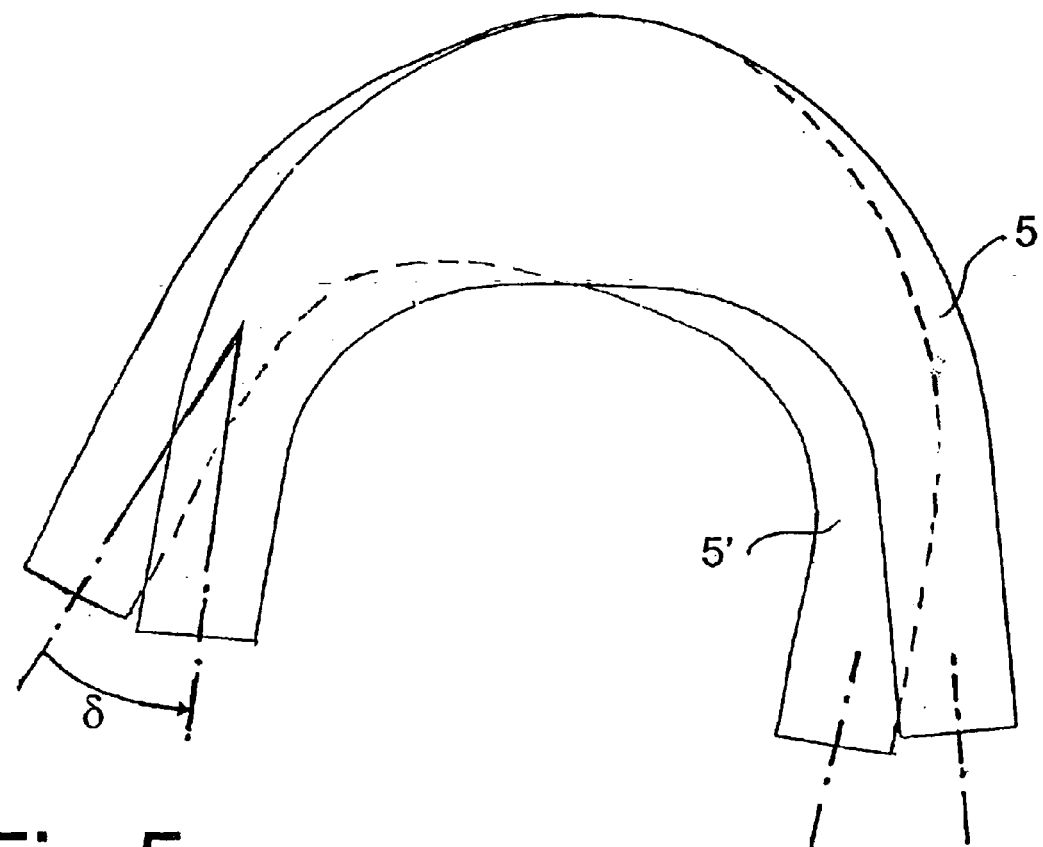
FIG. 5 is a diagrammatic plan view of a staggered arrangement of two sacs.

To render the housing 1 low-profile, the two sacs 5, 5' can be staggered relative to each other by an angle δ (see FIG. 5). Furthermore, the sacs 5, 5' are accommodated in the housing 1 so that no backflow of fluid (blood) can occur in the inlet or outlet region. The sacs 5, 5' are made of a highly elastic material to thus achieve enhanced flow-mechanical properties and, more particularly, to damp pressure surges.

Figure 6:
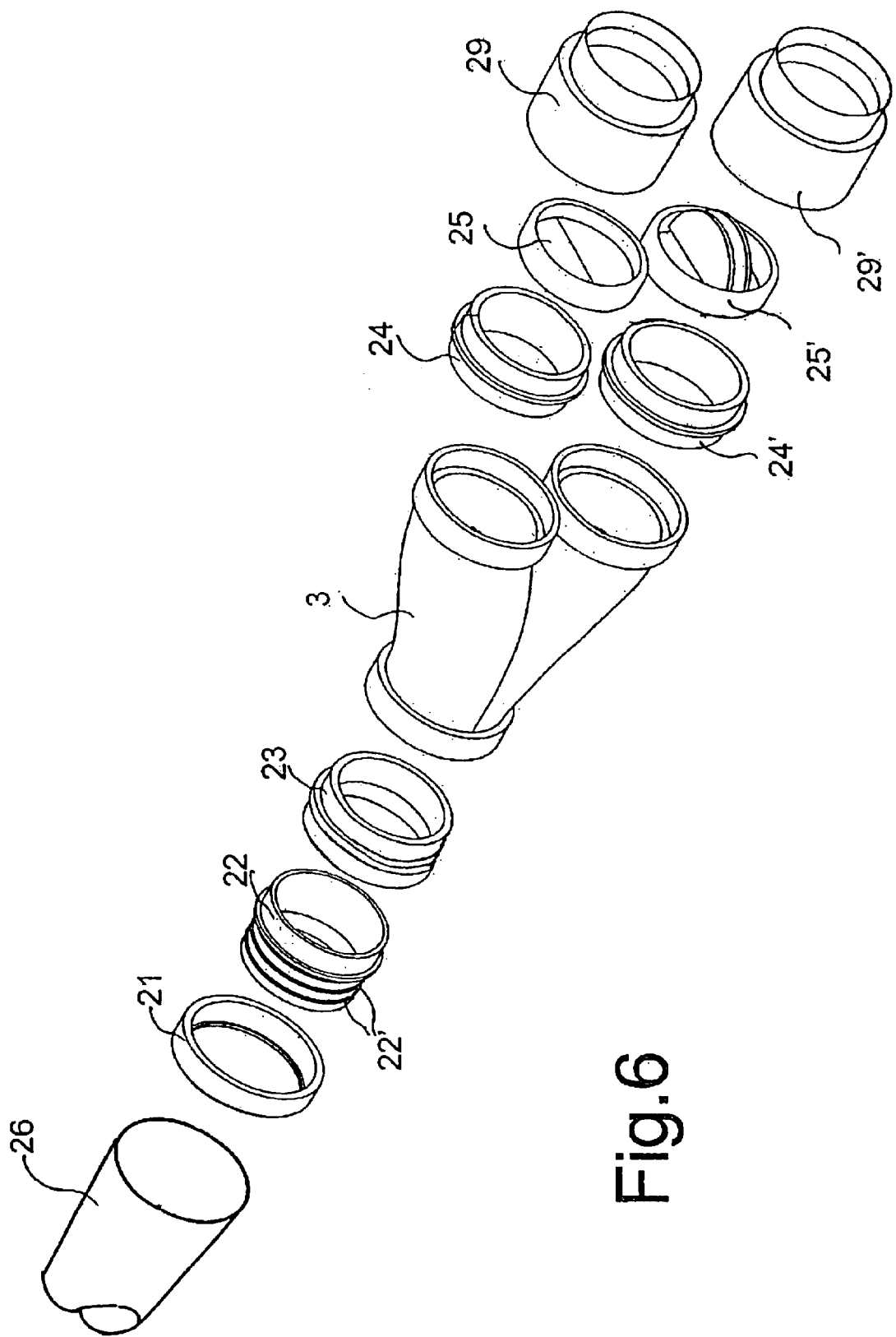
FIG. 6 is a view in perspective of a Y-shaped adapter including adapter parts assigned thereto for dividing a fluid flow to the two sacs of a pumping means.

Referring now to FIG. 6 there is illustrated the Y-shaped adapter 3, the adapter parts assigned thereto and two aortic valve prosthetics 25, 25' all in a view in perspective. A tube 26 coming from the heart is mounted on an adapter part 22 where it is located in place, for example, by means of a bonded joint. Low circular ridges or threads 22' are provided at the outer circumference of the adapter part 22 to boost the tensile strength as well as to seal off the connection.

In the Y-shaped adapter 3 at the inlet side an adapter part 23 is fitted and at the end of the branches thereof adapter parts 24 and 24' respectively are fitted. Mounted in the tubular ports 10a and 10a' of the housing halves 10 and 10' are adapter parts 29 and 29' respectively in which fittings are configured fur mounting the aortic valve prosthetics 25 and 25'.

Once the pumping means has been fitted and both housing halves 10, 10' of the housing 1 joined together, the aortic valve prosthetics 25, 25' are inserted into the adapter parts 29 and 29' respectively, after which the Y-shaped adapter 3 with the inserted adapter parts 24 and 24' respectively is inserted in the adapter parts 29 and 29' respectively of the housing 1. This results in the aortic valve prosthetics 25, 25' being axially defined and the pumping means assembled at the inlet side.

When the pump is connected to a living heart, first one end of the tube 26 is attached to the heart. The adapter part 22 secured to the other end of the tube 26 is inserted into the adapter part 23 and locked in place by means of a sleeve nut 21.

Figure 7:
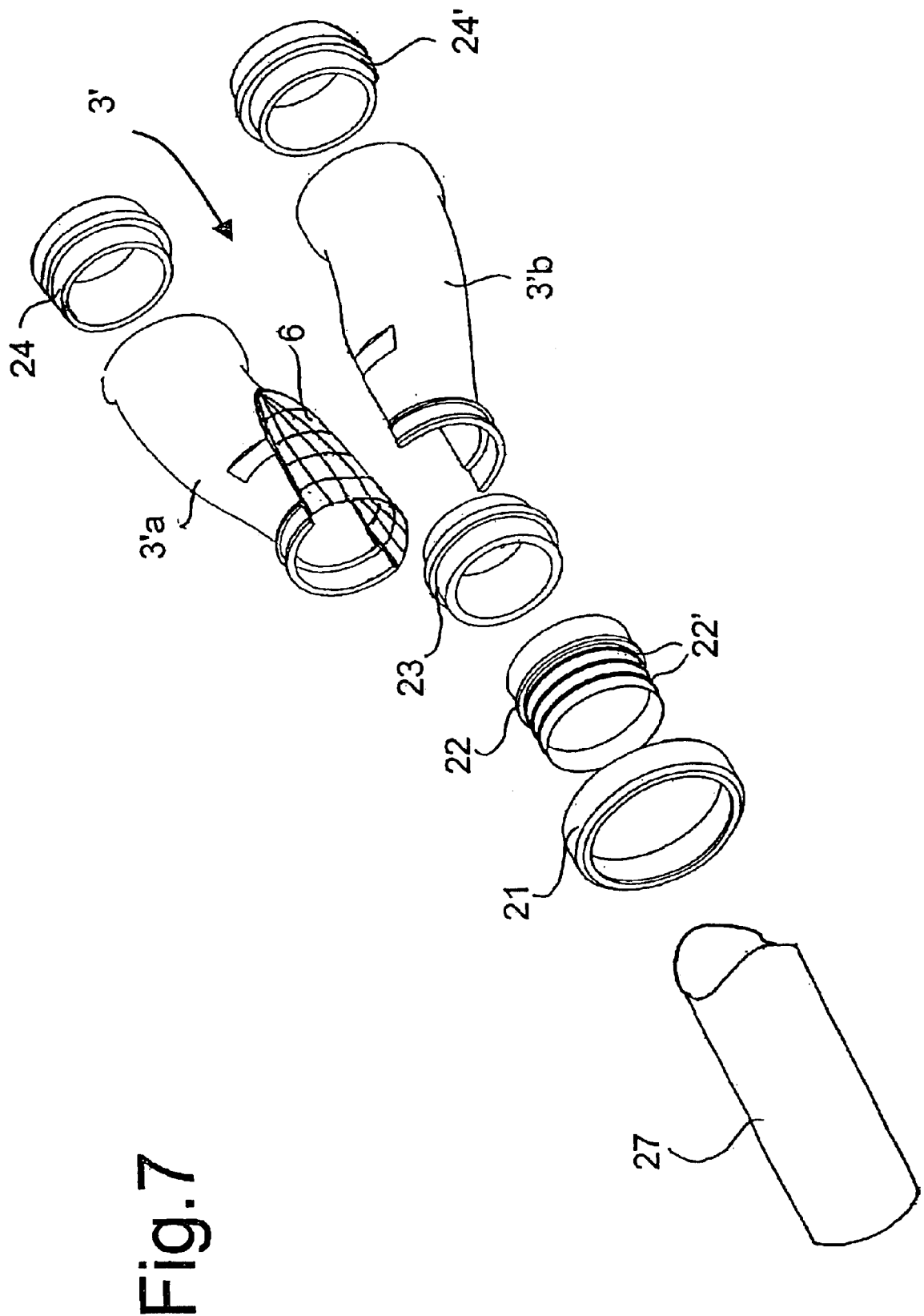
FIG. 7 is a view in perspective of a further Y-shaped adapter with a integrated sail valve for merging the fluid flows coming from the two sacs of the pumping means.

Referring now to FIG. 7 there is illustrated a Y-shaped adapter 3' with the integrated sail valve 6 shown in two halves for a better appreciation. Expediently, however, the Y-shaped adapter 3' is configured in one piece. The sail valve 6 begins at the branching point of the substantially identical halves 3a' and 3'b of the Y-shaped adapter 3' and extends up to the outlet portion thereof. The sail valve 6 is made of a very thin, flexible organic or inorganic material. The Y-shaped adapter 3' with the inserted adapter parts 23 and 22 is pushed into the tubular ports 10b and 10'b of the assembled housing 1 and sealed in place.

When the pump is connected to a living hearrt, first one end of the tube 27 is attached to the heart or aorta. The adapter part 22 secured to the other end of the tube 27 is inserted into the adapter part 23 and located in place by means of a sleeve nut 21, for example. The annular ridges or threads 22' at the outer circumference of the adapter part 22 boost the tensile strength and improve the seal of the connection.

To move the pusher plate 8 between the end positions A, B (see FIG. 3) a drive unit 41 in the form of a geared electric motor is provided.

Rotation of the drive unit 41 is communicated to an eccentric cam 44. Mounted at the eccentric cam 44 is a connecting rod 42, by means of which the rotation of the eccentric cam 44 is communicated to a lever arm 43 whose other end is rigidly connected to a shaft. It is to this shaft that two lever arms 49 preferably identical in length are rigidly connected preferably at an angle of 90° relative to the lever arm 43.

On every rotation of the cam 44 the pusher plate 8 is moved between the end positions A, B by the lever arm 43 and lever arms 49 rigidly connected to the shaft. As stated above, the angle between the lever arm 43 and the arms 49 is preferably 90°. When the angles between the lever arm 43 and the two arms 49 differ, the sacs 5, 5' are differeingly compressed by the pusher plate 8.

Figure 9:
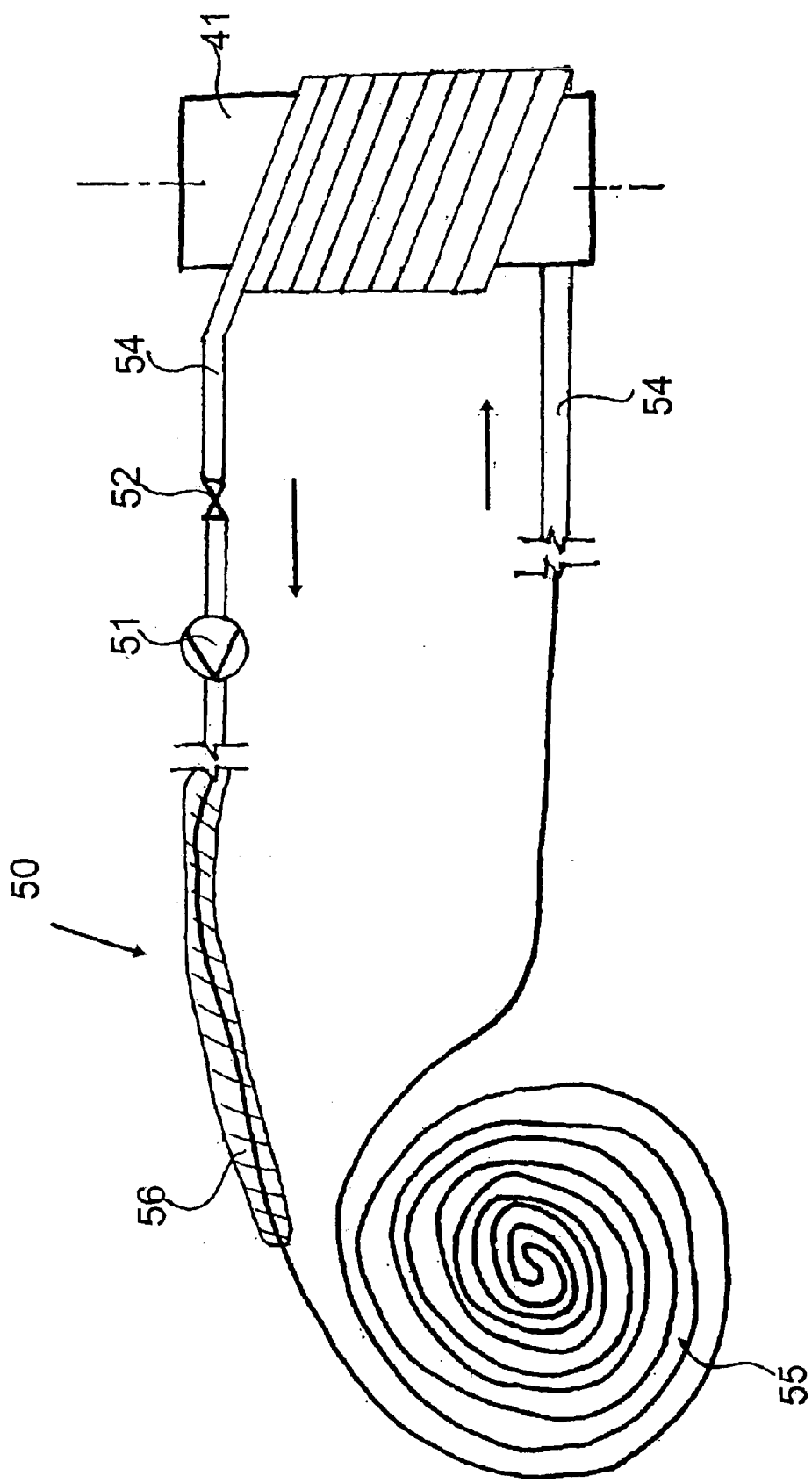
FIG. 9 is a diagrammatic view of an implantable cooling means for cooling a drive unit and FIG. 10 is a diagrammatic view of an implantable power supply means for a ventricle assist system as well as an extracorporeal power supply means.

Referring now to FIG. 9 there is illustrated an embodiment of a cooling means 50 for the drive unit 41. The element to be cooled, in this case the drive unit 41, is surrounded by closely juxtaposed windings of an endless tube 54 which are preferably fixedly connected to the drive unit 41, for example, by bonded connections; although several plies of windings may also be provided.

The remaining tube 54 is led to a location provided for cooling where it is located in place in the form of an endless coil 55; for this purpose the windings of the coil 55 are potted with a suitable material.

So that a cooling agent can circulate in the tube 54 a pump 51 is integrated in the closed circuit. In FIG. 9 a displacement pump including a check valve 52 is provided as the pump. When used as a blood pump, tubing and materials of biocompatble substances, such as, for example, medical silicone or polyurthane, are employed.

With the aid of the pump 51 the cooling agent is circulated in the tube 54. To prevent heat already being given off prior to attaining the coil 55, the tube 54 is sheathed from the drive unit 41 up to the coil 55 with a corresponding insulation 56. Pump 51 and check valve 52 may also be accommodated in the cooling side of the circuit, i.e. in the inflow to the element 41 to be cooled.

When employing, for example, an axial pump the check valve can be eliminated. Where necessary, the pusher plate 8 may also be used in such a way that a portion of the tube 54 is pinched like a peristaltic pump in thereby delivering the cooling agent.

Since the tube 54 surrounds the drive unit 41 to be cooled in closely juxtaposed windings, the cooling agent receives and carries away the heat from the warm unit 41 via the surface of the tubing. How good this transition is depends, among other things, on the coefficient of heat transfer of the tube 54 and that of the connection between tube and drive unit 41, the diameter and wall thickness of the tube, the number of windings as well as on the flow rate of the cooling agent.

The pump 51 returns the cooling agent back to the windings surrounding the drive unit 41. Pump 51 and check valve 52 may also be accommodated, where necessary, in the housing of an electronic controller The cooling means can be incorporated in fatty tissue, where necessary, just beneath the skin so that greater fluctuations in temperature have a less drastic effect on the organism as a whole and the heat, for example of the drive unit 41, can be optimally removed.

Figure 10:
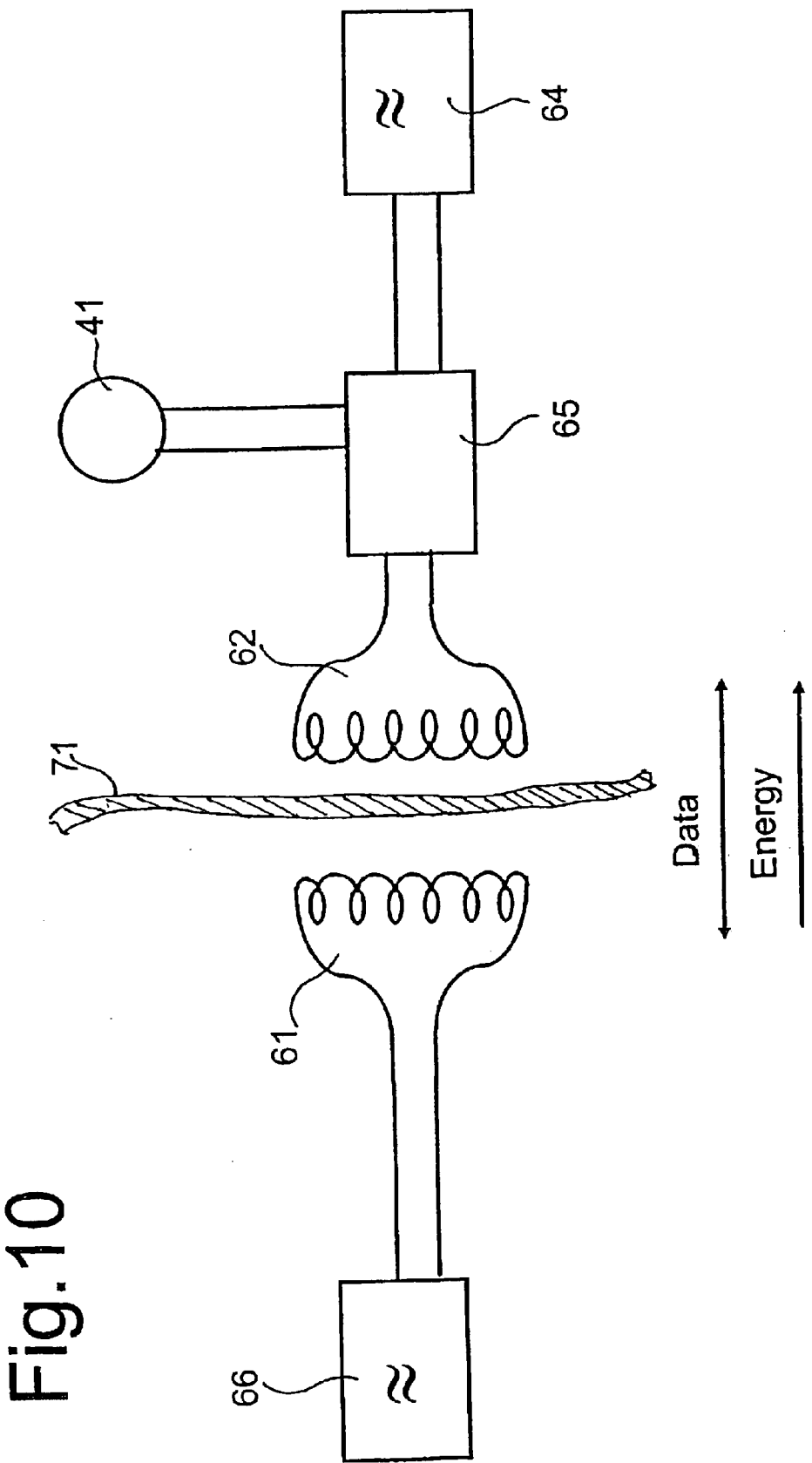

Referring now to FIG. 10 there is illustrated an implantable power supply unit 60 via which the drive unit 41 can be powered and simultaneously data communicated.

The power supply unit 60 comprises a miniature encapsulated power reservoir 64 including an electronic controller wired to the drive unit 41. For charging the miniature power reservoir 64 it is connected via a charging regulator 65 to an induction coil 62 implantable in the body of the patient. Preferably the induction coil 62 is provided in the fatty tissue just beneath the skin 71. A second induction coil 61 connected to a larger power reservoir 66 is provided extracorporeal.

For communicating energy from the extracorporeal power reservoir 66 to the smaller power reservoir 64 the induction coil 61 is positioned precisely opposite the induction coil 62 implanted under the skin 71. An AC voltage is applied to the induction coil 61 to induce voltage in the implanted induction coil 62. This induced voltage is used to charge the implanted power reservoir 64 at the charging regulator 65. With the miniature power reservoir 64 an energy buffer is thus available so that for a certain period of time the power supply for operating the pumping means is assured even when the extracorporeal power supply is briefly disconnected.

By superimposing a high-frequency AC voltage on the power AC data can be communicated via the induction coils 61, 62 as may be needed as command, diagnostic, status, control signals and the like.

The miniature power reservoir 64 can also be monitored so that a corresponding status alert is output as soon as a defined charging level is fallen short of. Since the implanted miniature power reservoir 64 can become exhausted relatively quickly when the extracorporeal power reservoir 66 is disconnected, this would inevitably result in the pumping means failing, should the condition go unnoticed. This is why as soon as a critical minimum charging level is fallen short of, an alert, for example in the form of a beeper signal, is output and/or a signal is sent to an external detector or a combination of various alert signals may be provided.

What is claimed is:

1. An implantable system for assisting the left heart ventricle, said system comprising: a pumping means including a drive unit; a cooling means for cooling said drive unit; and a power supply unit for said cooling means and said drive unit, wherein:

said pumping means comprises two compressible pump chambers constituted by sacs and a single pusher plate arranged between said two pump chambers, said pusher plate being movable back and forth between two end positions by operation of said drive unit in order to compress said two pump chambers in alternation;

each of said pump chambers has an inlet side and an outlet side and one of said two pump chambers is emptied while the other one is being filled, and vice versa; and said system further comprises:

two inlet side adapter parts and two heart valves, each said heart valve being housed in a respective adapter part and each said inlet side adapter part being connected to the inlet side of a respective pump chamber;

a first Y-adapter having two branches each connected to a respective inlet side adapter part;

two outlet side adapter parts each connected to the outlet side of a respective pump chamber;

a second Y-adapter having two branches each connected to a respective outlet side adapter part; and a flap-shaped sail valve housed in said second Y-adapter at a location where said branches of said second Y-adapter meet.

2. The system as set forth in claim 1, wherein said sail valve consists of a thin, flexible material.

3. The system as set forth in claim 1, wherein said compressible pump chambers are arranged one above the other precisely or slightly staggered.

4. The system as set forth in claim 3, wherein said compressible pump chambers are curved and have a steadily increasing diameter from a diameter ($D_1$) at the inlet side to a maximum diameter (Dmax) and subsequently have a steadily decreasing diameter to a diameter ($D_2$) at the outlet side.

5. The system as set forth in claim 4, wherein the diameters (D1, D2) at the inlet side and outlet side are identical.

6. The system as set forth in claim 4, wherein the diameter (D1) at the inlet side is larger than the diameter (D2) at the outlet side.

7. The system as set forth in claim 1, further comprising a two-part housing having tubular ports, wherein said pumping means, said drive unit and a portion of said cooling means are accommodated in said two-part housing said Y-shaped adapter elements extend through said tubular ports.

8. The system as set forth in claim 1, wherein said drive unit comprises a geared electric motor having a drive shaft and a mechanism coupled to said drive shaft and said pusher plate for converting rotation of said drive shaft into a back and forth swinging movement of said pusher plate.

9. The system as set forth in claim 1, wherein said cooling means comprises an endless tube filled with a cooling agent, part of said endless tube is wound into a number of windings surrounding said drive unit for cooling said drive unit, and a further part of said endless tube is operative for cooling the cooling agent and is arranged in a tightly wound spiral arrangement directly under the skin of the implant patient.

10. The system as set forth in claim 1, wherein said power supply unit comprises: a small power reservoir; a first induction coil for charging said small power reservoir and arranged under the skin of the implant patient; and a charging regulator connected between said small power reservoir and said first induction coil for controlling and monitoring charging of said small power reservoir.

11. The system as set forth in claim 10, wherein said power supply unit further comprises: a larger power reservoir provided extracorporeally; and a second induction coil provided extracorporeally next to said first induction coil for power transmission to said first induction coil.

* * * * *